US012799095B2

(12) United States Patent
Iuvone et al.

(10) Patent No.: US 12,799,095 B2
(45) Date of Patent: Nov. 17, 2026

(54) N-ACETYLSEROTONIN DERIVATIVES AS TRKB ACTIVATORS AND USES THEREOF

(71) Applicant: Emory University, Atlanta, GA (US)

(72) Inventors: Paul Michael Iuvone, Decatur, GA (US); Frank Edward McDonald, Tucker, GA (US); Christopher Lee Walker, Loganville, GA (US)

(73) Assignee: Emory University, Atlanta, GA (US)

(*) Notice: Subject to any disclaimer, the term of this patent is extended or adjusted under 35 U.S.C. 154(b) by 840 days.

(21) Appl. No.: 17/922,131

(22) PCT Filed: Apr. 29, 2021

(86) PCT No.: PCT/US2021/029908
§ 371 (c)(1),
(2) Date: Oct. 28, 2022

(87) PCT Pub. No.: WO2021/222577
PCT Pub. Date: Nov. 4, 2021

(65) Prior Publication Data

US 2023/0174510 A1 Jun. 8, 2023

Related U.S. Application Data

(60) Provisional application No. 63/017,383, filed on Apr. 29, 2020.

(51) Int. Cl.
*C07D 401/12* (2006.01)
*C07D 209/16* (2006.01)

(52) U.S. Cl.
CPC ......... *C07D 401/12* (2013.01); *C07D 209/16* (2013.01)

(58) Field of Classification Search
CPC ............................ C07D 209/16; C07D 401/12
See application file for complete search history.

(56) References Cited

U.S. PATENT DOCUMENTS

| | | | |
|---|---|---|---|
| 2009/0163545 | A1 | 6/2009 | Goldfarb |
| 2010/0297121 | A1 | 11/2010 | Mi |
| 2013/0196050 | A1 | 8/2013 | Amino |
| 2014/0323549 | A1 | 10/2014 | Feistein |
| 2016/0354465 | A1 | 12/2016 | Mi |
| 2017/0029511 | A1 | 2/2017 | Saragovi |

FOREIGN PATENT DOCUMENTS

| | | | | |
|---|---|---|---|---|
| CN | 1365971 | A | 8/2002 | |
| CN | 102816103 | | 12/2012 | |
| CN | 105198786 | A | 12/2015 | |
| DE | 3145465 | A * | 5/1983 | ........... C07D 209/16 |
| JP | 2009-501710 | A2 | 1/2009 | |
| WO | 2007133108 | | 12/2006 | |
| WO | 2012042621 | A1 | 4/2012 | |

OTHER PUBLICATIONS

RN 1928847-53-3, STN entry (see page of STN search), Jun. 2016.*
Karoutzou et al., ChemistrySelect, 2019, 4, 8724-8730.*
Schuck et al. Eu J Med Chem, 78, 2014, 375-382.*
Liang et al. Tetrahedron, 56, 2015, 2466-2468.*
Merriam-Webster: "preventing", 1 pg.*
RN 29745-41-3, registration date of 1984, 1 pg.*
Shen et al., PNAS, 109, 9, 2012, 3540-6545.*
Boatright et al. Novel Method for Determining Retinal Ganglion Cell Loss 2013 ISER Sarasota Symposium, Poster Abstracts.
CAS, 3-Piperidinecarboxamide, N-[2-(5-methoxy-1H-indol-3-yl)ethyl]-3-methyl-, hydrochloride (1:1) (ACI), Component RN: 1570584-06-3, American Chemical Society.
Iuvone et al. N-Acetylserotonin: Circadian Activation of the BDNF Receptor and Neuroprotection in the Retina and Brain, Adv Exp Med Biol. 2014, 801: 765-771.
Juvone et al. Protection from blast-induced vision loss by the N-acetylserotonin derivative HIOC through a BDNF/TrkB receptor mechanism, Investigative Ophthalmology & Visual Science, 2016, vol. 57, 737.
May et al. The epidemiology of serious eye injuries from the United States Eye Injury Registry, Graefe's Arch Clin Exp Ophthalmol (2000) 238:153-157.
Pubchem, (3-[2-(Benzoylamino)ethyl]-1H-indole-5-ol), SID 108666612, available at http://pubchem.ncbi.nih.gov/substance/108666612.
Setterholm et al. Gram-scale, chemoselective synthesis of N-[2-(5-hydroxy-1Hindol-3-yl)ethyl]-2-oxopiperidine-3-carboxamide (HIOC), Tetrahedron Lett. 2015, 56(23): 3413-3415.
Shen et al. N-acetyl serotonin derivatives as potent neuroprotectants for retinas, PNAS, 2012,vol. 109, No. 9, 3540-3545.
Struebing et al. Transcriptional Changes in the Mouse Retina after Ocular Blast Injury: A Role for the Immune System, Journal of Neurotrauma 35:118-129 (2018).
Tang et al. Neuroprotective Role of an N-acetyl Serotonin Derivative via Activation of Tropomyosin-related Kinase Receptor B after Subarachnoid Hemorrhage in a Rat Model, Neurobiol Dis. 2015, 78: 126-133.
Yamada et al. novel synthesis of 3,4,5,6-tetrahydro-7-hydroxy-1H-azepino[5,4,3-cd] indole derivatives from serotonin1, Heterocycles, 2011, 83,(11):2547-2562.
Yamazaki, et al. "N-[(Dihydroxyphenyl)acyl]serotonins as potent inhibitors of tyrosinase from mouse and human melanoma cells", Bioorganic & Medicinal Chemistry Letters, vol. 19, No. 15, (2009), pp. 4178-4182.

(Continued)

*Primary Examiner* — Kyle A Purdy
(74) *Attorney, Agent, or Firm* — THOMAS | HORSTEMEYER, LLP

(57) ABSTRACT

This disclosure relates to N-acetylserotonin derivatives that have neuroprotective properties for uses in treating or preventing traumatic brain injury, vision loss, neuronal cell ischemia, and retinal degenerative diseases. In certain embodiments, this disclosure relates to pharmaceutical compositions comprising the N-acetylserotonin derivative and a pharmaceutically acceptable excipient.

3 Claims, 4 Drawing Sheets

(56) References Cited

OTHER PUBLICATIONS

Gozzo, et al. "Structure-activity relationships in a series of melatonin analogues with the low-density lipoprotein oxidation model", Free Radical Biology & Medicine, vol. 26, Nos. 11-12, (1999), pp. 1538-1543.
Szumilo, et al. "Demonstration of Tryptamide and its Metabolites with Solid Phase Extraction, TLC, and HPLC in Rats", Journal of Liquid Chromatography, vol. 15, No. 2, (1992), pp. 337-349.
European Extended Search Report, EP Application No. 21795434.6, mailed Apr. 16, 2024.
Database Registry, 2019, RN 2345241-15-6, RN 2345241-14-5, RN 1904516-81-9, RN 1052507-85-3, Retrieved from STN international [online]; retrieved on Sep. 17, 2025.
Hanna-Elias, et al., Synthesis, Testing and Structure-Activity Studies on a Library of 5-HT4 Ligands, Medicinal Chemistry, 2010, vol. 6, pp. 344-354.
Kozono et al., Roles of the serotonin 5-HT4 receptor in dendrite formation of the rat hippocampal neurons in vitro, Brain Research, 2017, vol. 1655, pp. 114-121.
Pharmaceutics and Physical Pharmacy, 2012, pp. 259 to 266.
Thoai et al., Design and Synthesis of Sustain-Acting Melatonin Prodrugs, Journal of Chemistry ,2013 , Article ID 684760, 6 pages.
Malik et al., Hydrophilic Prodrug Approach for Reduced Pigment Binding and Enhanced Transscleral Retinal Delivery of Celecoxib, Molecular Pharmaceutics, 2012, vol. 9, pp. 605-614.

* cited by examiner serotonin

HIOC (1)

2 methyl series (3)

$R^1$, $R^2$, $R^3$, $R^4$, or $R^5$ = $CH_3$

4

5

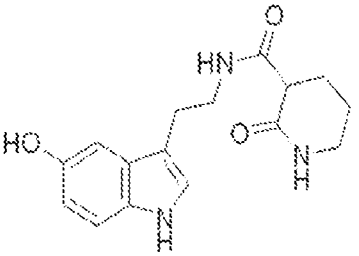

N-(2-(5-hydroxy-1H-indol-3-yl)ethyl)-2-oxopiperidine-3-carboxamide

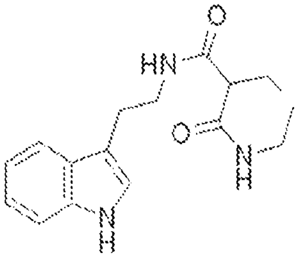

N-(2-(1H-indol-3-yl)ethyl)-2-oxopiperidine-3-carboxamide

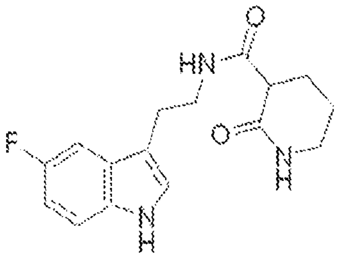

N-(2-(5-fluoro-1H-indol-3-yl)ethyl)-2-oxopiperidine-3-carboxamide

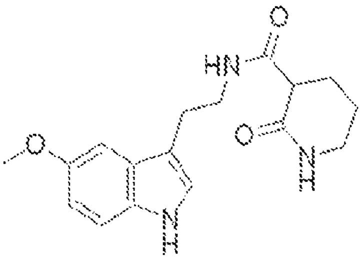

N-(2-(5-methoxy-1H-indol-3-yl)ethyl)-2-oxopiperidine-3-carboxamide

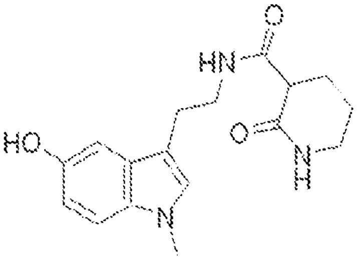

N-(2-(5-hydroxy-1-methyl-1H-indol-3-yl)ethyl)-2-oxopiperidine-3-carboxamide

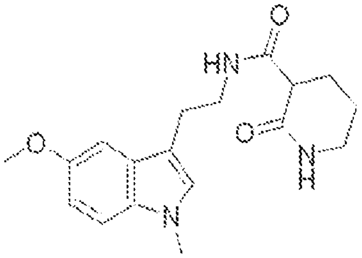

N-(2-(5-methoxy-1-methyl-1H-indol-3-yl)ethyl)-2-oxopiperidine-3-carboxamide

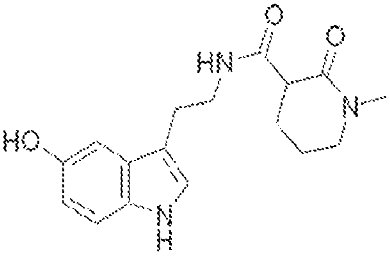

N-(2-(5-hydroxy-1H-indol-3-yl)ethyl)-1-methyl-2-oxopiperidine-3-carboxamide

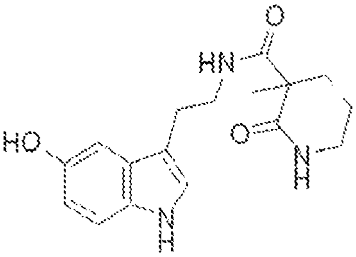

N-(2-(5-hydroxy-1H-indol-3-yl)ethyl)-3-methyl-2-oxopiperidine-3-carboxamide

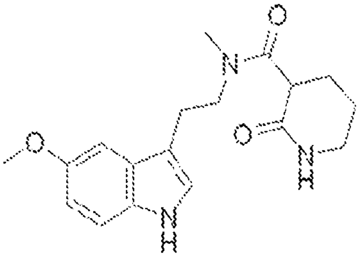

N-(2-(5-methoxy-1H-indol-3-yl)ethyl)-N-methyl-2-oxopiperidine-3-carboxamide

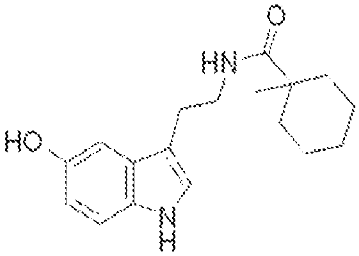

N-(2-(5-hydroxy-1H-indol-3-yl)ethyl)-1-methylcyclohexane-1-carboxamide

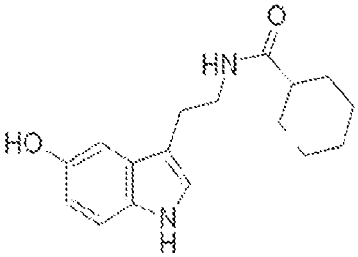

N-(2-(5-hydroxy-1H-indol-3-yl)ethyl)cyclohexanecarboxamide

FIG. 3

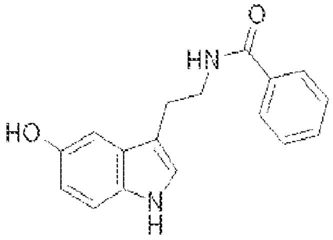

N-(2-(5-hydroxy-1H-indol-3-yl)ethyl)benzamide

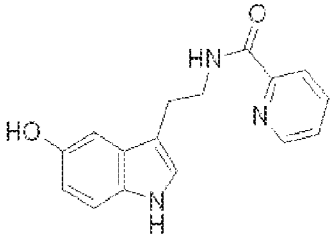

N-(2-(5-hydroxy-1H-indol-3-yl)ethyl)picolinamide

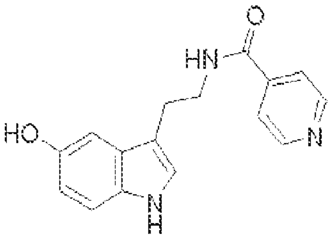

N-(2-(5-hydroxy-1H-indol-3-yl)ethyl)isonicotinamide

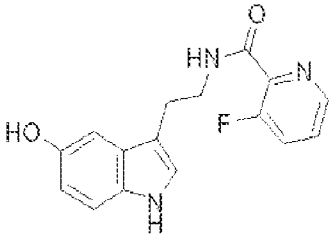

3-fluoro-N-(2-(5-hydroxy-1H-indol-3-yl)ethyl)picolinamide

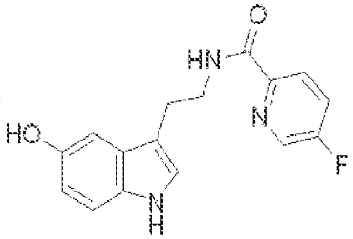

5-fluoro-N-(2-(5-hydroxy-1H-indol-3-yl)ethyl)picolinamide

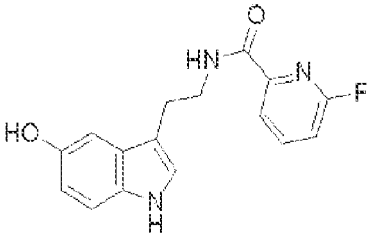

6-fluoro-N-(2-(5-hydroxy-1H-indol-3-yl)ethyl)picolinamide

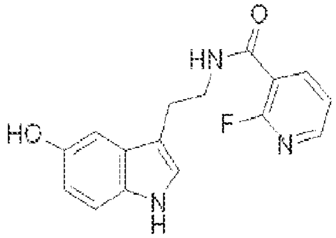

2-fluoro-N-(2-(5-hydroxy-1H-indol-3-yl)ethyl)nicotinamide

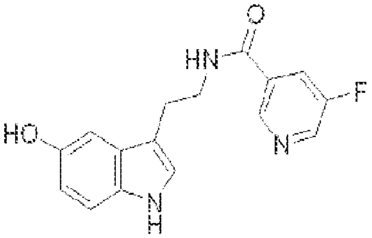

5-fluoro-N-(2-(5-hydroxy-1H-indol-3-yl)ethyl)nicotinamide

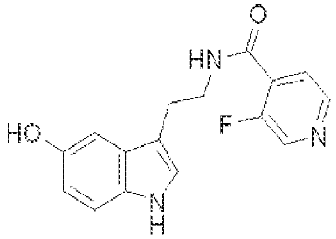

3-fluoro-N-(2-(5-hydroxy-1H-indol-3-yl)ethyl)isonicotinamide

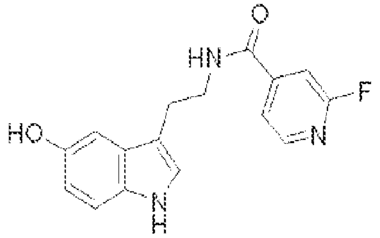

2-fluoro-N-(2-(5-hydroxy-1H-indol-3-yl)ethyl)isonicotinamide

FIG. 4

N-ACETYLSEROTONIN DERIVATIVES AS TRKB ACTIVATORS AND USES THEREOF

CROSS-REFERENCE TO RELATED APPLICATIONS

This application is the National Stage of International Application No. PCT/US2021/043017 filed Jul. 23, 2021, which claims the benefit of U.S. Provisional Application No. 63/017,383 filed Apr. 29, 2020. The entirety of each of these applications is hereby incorporated by reference for all purposes.

STATEMENT REGARDING FEDERALLY SPONSORED RESEARCH OR DEVELOPMENT

This invention was made with government support under W81XWH-12-1-0436 awarded by the Department of Defense and W81XWH-18-1-0700 awarded by the Department of Defense. The government has certain rights in the invention.

BACKGROUND

Traumatic blast injury from explosive devices is a common cause of craniomaxillofacial injuries. Traumatic blast injury frequently results in vision loss due to ocular damage and insult to the optic nerve or central visual pathways. In cases of traumatic blast-induced ocular injury, the retina may be directly damaged by the pressure waves from the explosion. In addition, traumatic optic neuropathy may be caused by several factors, including shear due to percussive forces or penetrating injury. Such damage is typically not preventable with current therapies. Additional causes of optic neuropathy resulting in vision loss from blunt force trauma include automobile accidents, sports injuries, and first fights. A therapy is needed to slow or prevent trauma-induced neuronal degeneration in the retina and central visual pathways.

Tropomyosin-related kinase B (TrkB), a tyrosine kinase receptor, is the cognate receptor for Brain-Derived Neurotrophic Factor (BDNF). After ocular hypertension BDNF is upregulated. BDNF promotes TrkB phosphorylation and activation of a cell survival signaling pathway. Iuvone et al. report N-[2-(5-hydroxy-1H-indol-3-yl)ethyl]-2-oxopiperidine-3-carboximide (HIOC), selectively activates TrkB and reduces kainic acid-induced neuronal cell death in a TrkB-dependent manner. Adv Exp Med Biol. 2014, 801:765-771.

References cited herein are not an admission of prior art.

SUMMARY

This disclosure relates to N-acetylserotonin derivatives that have neuroprotective properties for uses in treating or preventing traumatic brain injury, neuronal cell ischemia, and retinal degenerative diseases. In certain embodiments, the N-acetylserotonin derivative has the following formula:

Formula I

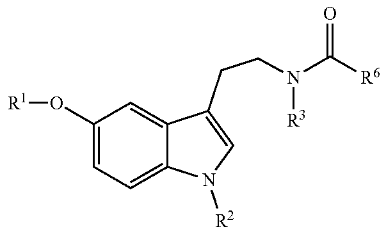

or

-continued

Formula II

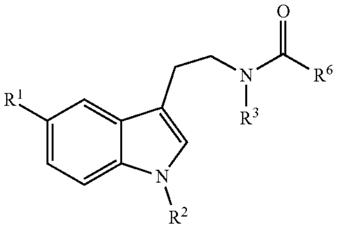

or salts thereof, wherein, $R^1$ is hydrogen, methyl, or alkyl; $R^2$ is hydrogen, methyl, or alkyl; $R^3$ is hydrogen, methyl, or alkyl; $R^6$ is 2-oxopiperidinyl, pyridinyl, cyclohexyl, or phenyl wherein $R^6$ is optionally substituted with a halogen, methyl, or alkyl. In certain embodiments, halogen is a fluoro.

In certain embodiments, this disclosure relates to pharmaceutical compositions comprising a therapeutically effective amount of an N-acetylserotonin derivative disclosed herein and a pharmaceutically acceptable carrier. In other embodiments, such pharmaceutical compositions are formulated as tablets, pills, capsules, a liquid, an inhalant, a nasal spray solution, a suppository, a solution, an emulsion, an ointment, eye drops or ear drops.

In certain embodiments, this disclosure relates to methods of treating or preventing vision loss comprising administering an effective amount of an N-acetylserotonin derivative disclosed herein to a subject that has experience a physical impact to the head or the eye. In certain embodiments, this disclosure relates to methods of treating or preventing ocular ischemic injury comprising administering an effective amount of an N-acetylserotonin derivative disclosed herein to a subject in need thereof. In certain embodiments, the ocular ischemic injury is injury to the retina, retinal blood vessels, or optic nerve.

In certain embodiments, this disclosure relates to methods of treating or preventing a TrkB-treatable disease or condition comprising administering an effective amount of an N-acetylserotonin derivative disclosed herein to a subject in need thereof. In certain embodiments, the subject is at risk of, suspected of having or diagnosed with a TrkB-treatable disease or condition. In certain embodiments, the TrkB-treatable disease or condition is optic neuropathy, a neurological disorder, an autoimmune disorder, autoimmune encephalomyelitis, multiple sclerosis, immune rejection, inflammatory bowel disease, Huntington's disease, Alzheimer's, disease, or Parkinson's disease. In preferred embodiments, the subject is a human.

In certain embodiments, this disclosure contemplates that N-acetylserotonin derivative disclosed herein and pharmaceutical compositions comprising the same are administered topically or locally to the eye (i.e., subconjunctival, intravitreal, retrobulbar, intracameral, intravitreal injections/implants and periocular injections), and/or systemically. In certain embodiments, this disclosure contemplates administration as a cream, an ointment, or a liquid drop preparation in the conjunctival sac. In certain embodiments, this disclosure contemplates systemic or oral delivery alone or in combination with topical delivery.

In certain embodiments, this disclosure relates to a medicament for treating a TrkB-treatable disease or condition in a patient comprising a therapeutically effective amount of an N-acetylserotonin derivative disclosed herein. In certain embodiments, this disclosure relates to the use of an N-acetylserotonin derivative disclosed herein in the manufacture of a medicament for treating a TrkB-treatable disease or condition.

BRIEF DESCRIPTION OF THE DRAWINGS

FIG. 3 illustrates embodiments of this disclosure.

FIG. 4 illustrates embodiments of this disclosure.

DETAILED DESCRIPTION

Figure 1:
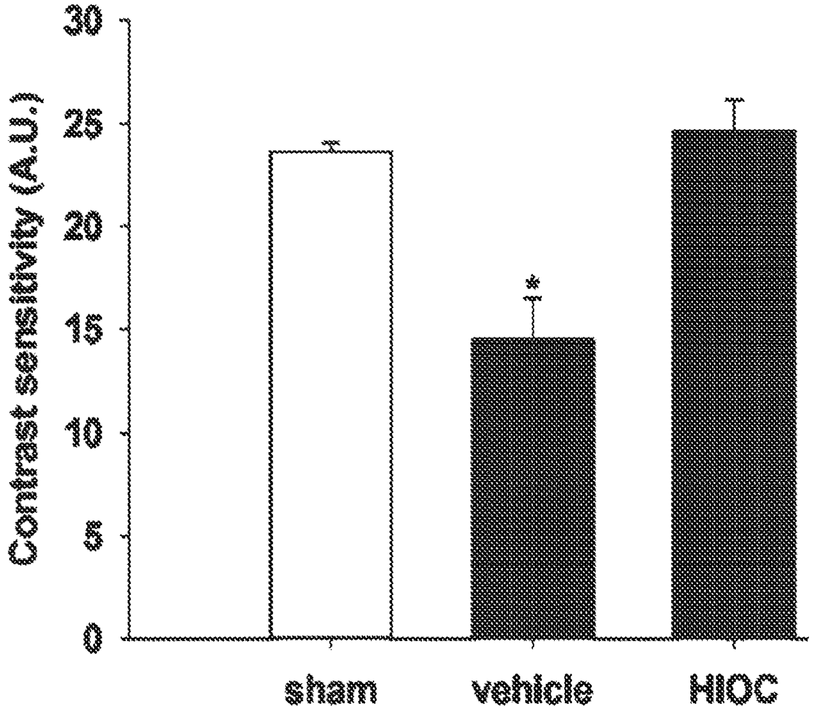
FIG. 1 shows data on the effect of HIOC on TBI-induced loss of visual function. Mice were exposed to a single 70 psi blast directed at the right side of the head. HIOC or vehicle was administered 15 minutes after exposure to blast, and daily for the next six days. A sham control group was included for comparison. Visual function was tested 1 week after blast.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Prior to describing the various embodiments, the following definitions are provided and should be used unless otherwise indicated. Further, headings provided herein are for convenience only and do not interpret the scope or meaning of the claims.

The compounds of the present disclosure may form one or more salts, tautomers, solvates, or contain one or more chiral centers and exist in different optically active forms. When the compound contains one chiral center, the compound comprises an enantiomer. The present disclosure includes mixtures of salts, stereoisomers, enantiomers, diastereomers, tautomers, or solvates. Enantiomers can be resolved by methods known in the art, such as crystallization, chiral chromatography and the like. When the compound contains more than one chiral centers, diastereomers may be present. The present disclosure includes specific optically pure isomers which have been resolved, as well as mixtures of diastereomers. Diastereomers can be resolved by methods known in the art, such as crystallization and preparative chromatography.

Unless the context requires otherwise, throughout the specification and claims which follow, the word "comprise" and variations thereof, such as, "comprises," "comprising" "including," "containing," or "characterized by," are to be construed in an open, inclusive sense, that is, as "including, but not limited to" and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical or other agent across a tissue layer.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. The salts can be prepared in situ during the isolation and purification of the compounds of the disclosure, or separately by reacting the free base or free acid of a compound of the disclosure with a suitable base or acid, respectively. Examples of pharmaceutically acceptable, nontoxic acid addition salts are salts of an amino group formed with inorganic acids such as hydrochloric acid, hydro bromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactate, laurate, lauryl sulfate, malate, maleate, malonate, methane-sulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkylsulfonate and aryl sulfonate.

As used herein, the term "derivative" refers to a structurally similar compound that retains sufficient functional attributes of the identified analogue. The derivative may be structurally similar because it is lacking one or more atoms, substituted, a prodrug, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optional has one or more substitutions. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, "alkyl" means a noncyclic straight chain or branched, unsaturated or saturated hydrocarbon such as those containing from 1 to 6 ($C_1$-$C_6$) or 1 to 10 ($C_1$-$C_{10}$) carbon atoms. A "higher alkyl" refers to unsaturated or saturated hydrocarbon having 6 or more carbon atoms. A "$C_8$-$C_{18}$" refers to an alkyl containing 8 to 18 carbon atoms. Likewise, a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" is employed herein to refer to those agents of interest/compounds, salts, compositions, dosage forms, etc., which are suitable for use in contact with the tissues of human beings and/or other mammals without excessive toxicity, irritation, allergic response, or other problem or complication, commensurate with a reasonable benefit/risk ratio. In some respects, pharmaceutically acceptable means approved by a regulatory agency of the federal or a state government, or listed in the U.S. Pharmacopeia or other generally recognized pharmacopeia for use in mammals (e.g., animals), and more particularly, in humans.

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

As used herein, "pharmaceutical formulation" and "pharmaceutical composition" can be used interchangeably.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

N-Acetylserotonin Derivatives

In certain embodiments, this disclosure relates to N-acetylserotonin derivative. In certain embodiments, the N-acetylserotonin derivative is a compound disclosed herein substituted with one or more, the same or different substituents, or salts thereof. In certain embodiments, the N-acetylserotonin derivative has the following formula I:

Formula I

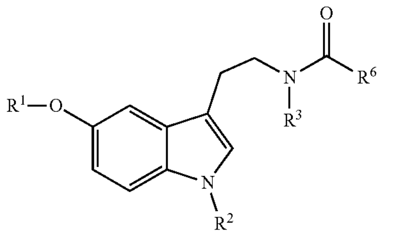

or salts thereof, wherein, $R^1$ is hydrogen, methyl, or alkyl; $R^2$ is hydrogen, methyl, or alkyl; $R^3$ is hydrogen, methyl, or alkyl; $R^6$ is 2-oxopiperidinyl, pyridinyl, cyclohexyl, or phenyl wherein $R^6$ is optionally substituted with a halogen, methyl, or alkyl. In certain embodiments, $R^1$ is methyl; $R^2$ is hydrogen, methyl, or alkyl; $R^3$ is hydrogen, methyl, or alkyl; $R^6$ is 2-oxopiperidinyl, pyridinyl, cyclohexyl, or phenyl wherein $R^6$ is optionally substituted with a halogen, methyl, or alkyl. In certain embodiments, $R^1$ is methyl or alkyl.

In certain embodiments, the N-acetylserotonin derivative has the following formula IA:

Formula IA

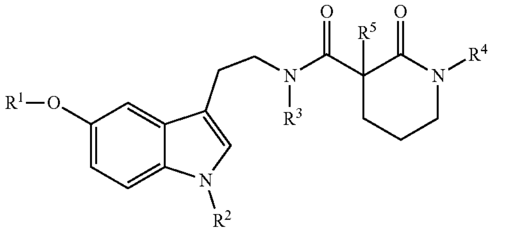

or salts thereof, wherein, $R^1$ is hydrogen, methyl, or alkyl; $R^2$ is hydrogen, methyl, or alkyl; $R^3$ is hydrogen, methyl, or alkyl; $R^4$ is hydrogen, methyl, or alkyl; $R^5$ is hydrogen, methyl, or alkyl. In certain embodiments, $R^1$ is methyl; $R^2$ is hydrogen, methyl, or alkyl; $R^3$ is hydrogen, methyl, or alkyl; $R^4$ is hydrogen, methyl, or alkyl; $R^5$ is hydrogen, methyl, or alkyl. In certain embodiments, it is provided that at least one $R^1$ to $R^5$ is methyl or alkyl. In certain embodiments, at least or only one $R^1$ to $R^5$ is methyl or alkyl wherein the other $R^1$ to $R^5$ are hydrogen.

In certain embodiments, the compound is selected from:

N-(2-(5-hydroxy-1H-indol-3-yl)ethyl)-2-oxopiperidine-3-carboxamide,

N-(2-(1H-indol-3-yl)ethyl)-2-oxopiperidine-3-carboxamide,

N-(2-(5-fluoro-1H-indol-3-yl)ethyl)-2-oxopiperidine-3-carboxamide,

N-(2-(5-methoxy-1H-indol-3-yl)ethyl)-2-oxopiperidine-3-carboxamide,

N-(2-(5-hydroxy-1-methyl-1H-indol-3-yl)ethyl)-2-oxopiperidine-3-carboxamide,

N-(2-(5-methoxy-1H-indol-3-yl)ethyl)-N-methyl-2-oxopiperidine-3-carboxamide,

N-(2-(5-hydroxy-1H-indol-3-yl)ethyl)-1-methyl-2-oxopiperidine-3-carboxamide,

N-(2-(5-hydroxy-1H-indol-3-yl)ethyl)-3-methyl-2-oxopiperidine-3-carboxamide, and N-(2-(5-methoxy-1H-indol-3-yl)ethyl)-N-methyl-2-oxopiperidine-3-carboxamide, or salts thereof.

In certain embodiments, the N-acetylserotonin derivative has the following formula IB:

Formula IB

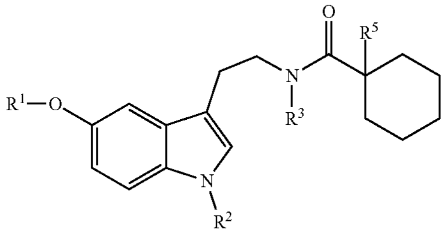

or salts thereof, wherein, $R^1$ is hydrogen, methyl, or alkyl; $R^2$ is hydrogen, methyl, or alkyl; $R^3$ is hydrogen, methyl, or alkyl; $R^5$ is hydrogen, methyl, or alkyl. In certain embodiments, $R^1$ is methyl; $R^2$ is hydrogen, methyl, or alkyl; $R^3$ is hydrogen, methyl, or alkyl; $R^5$ is hydrogen, methyl, or alkyl. In certain embodiments, it is provided that at least one $R^1$ to $R^5$ is methyl or alkyl. In certain embodiments as least or only one $R^1$ to $R^5$ is methyl or alkyl wherein the other $R^1$ to $R^5$ are hydrogen.

In certain embodiments, the compound is selected from: N-(2-(5-hydroxy-1H-indol-3-yl)ethyl)-1-methylcyclohexane-1-carboxamide and N-(2-(5-hydroxy-1H-indol-3-yl)ethyl)cyclohexanecarboxamide, or salts thereof.

In certain embodiments, the N-acetylserotonin derivative has the following formula IC:

Formula IC

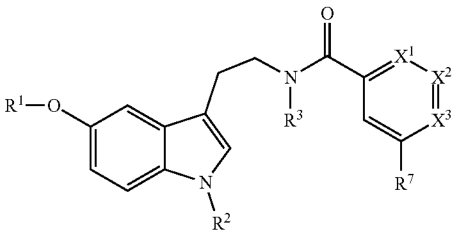

or salts thereof, wherein, $R^1$ is hydrogen, methyl, or alkyl; $R^2$ is hydrogen, methyl, or alkyl; $R^3$ is hydrogen, methyl, or alkyl; $R^7$ is hydrogen, or fluoro (F); $X^1$ is CH, CF, or N; $X^2$ is CH, CF, or N; $X^3$ is CH, CF, or N.

In certain embodiments, $X^1$ is CF.

In certain embodiments, $X^2$ is N.

In certain embodiments, $X^3$ is CH.

In certain embodiments, the compound is 2-fluoro-N-(2-(5-hydroxy-1H-indol-3-yl)ethyl) nicotinamide or salt thereof.

In certain embodiments, the compound is N-(2-(5-hydroxy-1H-indol-3-yl)ethyl)benzamide or salt thereof.

In certain embodiments, the compound is selected from:

N-(2-(5-hydroxy-1H-indol-3-yl)ethyl)benzamide,

N-(2-(5-hydroxy-1H-indol-3-yl)ethyl) picolinamide,

N-(2-(5-hydroxy-1H-indol-3-yl)ethyl) isonicotinamide, 3-fluoro-N-(2-(5-hydroxy-1H-indol-3-yl)ethyl) picolinamide, 5-fluoro-N-(2-(5-hydroxy-1H-indol-3-yl)ethyl) picolinamide,
6-fluoro-N-(2-(5-hydroxy-1H-indol-3-yl)ethyl) picolinamide,
2-fluoro-N-(2-(5-hydroxy-1H-indol-3-yl)ethyl) nicotinamide,
5-fluoro-N-(2-(5-hydroxy-1H-indol-3-yl)ethyl) nicotinamide,
3-fluoro-N-(2-(5-hydroxy-1H-indol-3-yl)ethyl) isonicotinamide, and
2-fluoro-N-(2-(5-hydroxy-1H-indol-3-yl)ethyl) isonicotinamide, or salts thereof.

In certain embodiments, the N-acetylserotonin derivative has the following formula II:

Formula II

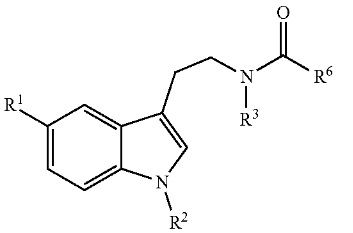

or salts thereof, wherein, $R^1$ is hydrogen; $R^2$ is hydrogen, methyl, or alkyl; $R^3$ is hydrogen, methyl, or alkyl; $R^6$ is 2-oxopiperidinyl, pyridinyl, cyclohexyl, or phenyl wherein $R^6$ is optionally substituted with a halogen, methyl, or alkyl. In certain embodiments, $R^1$ is hydrogen; $R^2$ is hydrogen, methyl, or alkyl; $R^3$ is hydrogen, methyl, or alkyl; $R^6$ is 2-oxopiperidinyl, pyridinyl, cyclohexyl, or phenyl wherein $R^6$ is optionally substituted with a halogen, methyl, or alkyl.

In certain embodiments, the N-acetylserotonin derivative has the following formula IIA:

Formula IIA

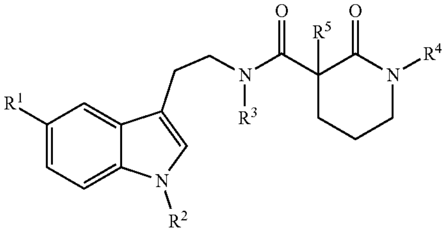

or salts thereof, wherein, $R^1$ is hydrogen; $R^2$ is hydrogen, methyl, or alkyl; $R^3$ is hydrogen, methyl, or alkyl; $R^4$ is hydrogen, methyl, or alkyl; $R^5$ is hydrogen, methyl, or alkyl. In certain embodiments, $R^1$ is hydrogen; $R^2$ is hydrogen, methyl, or alkyl; $R^3$ is hydrogen, methyl, or alkyl; $R^4$ is hydrogen, methyl, or alkyl; $R^5$ is hydrogen, methyl, or alkyl.

Methods of Use

Although it is not intended that embodiments of this disclosure be limited by any particular mechanism, it is believed that TrkB activation mitigates the effects of trauma. In certain embodiments, this disclosure relates to methods of treating or preventing vision loss comprising administering an effective amount of an N-acetylserotonin derivative disclosed herein to a subject that has experienced a physical impact to the head or the eye. In certain embodiments, this disclosure relates to methods of treating or preventing ocular ischemic injury comprising administering an effective amount of an N-acetylserotonin derivative disclosed herein to a subject in need thereof. In certain embodiments, the ocular ischemic injury is injury to the retina, retinal blood vessels, or optical nerve.

In certain embodiments, this disclosure relates to methods of treating or preventing a TrkB-treatable disease or condition comprising administering an effective amount of an N-acetylserotonin derivative disclosed herein to a subject in need thereof. In certain embodiments, the subject is at risk of, suspected of having or diagnosed with a TrkB-treatable disease or condition. In certain embodiments, the TrkB-treatable disease or condition is optic neuropathy, a neurological disorder, an autoimmune disorder, autoimmune encephalomyelitis, multiple sclerosis, immune rejection, inflammatory bowel disease, or Parkinson's disease. In preferred embodiments, the subject is a human.

In certain embodiments, this disclosure relates to methods of improving visual function such as contrast sensitivity and visual acuity/spatial frequency threshold comprising administering an N-acetylserotonin derivative disclosed herein to a subject in need thereof. In certain embodiments, the subject has military-relevant injuries.

In certain embodiments, this disclosure relates to methods of treating or preventing damage to ocular structures and the visual system consequent.

In certain embodiments, this disclosure relates to methods of treating or preventing injuries and diseases to ocular structures and visual systems including optic neuropathy, retinal injury, and ocular polytrauma.

In certain embodiments, this disclosure relates to methods of reducing vision loss, microglial activation in the retina, nerve fiber layer thinning, and the optic nerve axon loss, e.g., resulting from blast exposure.

In certain embodiments, this disclosure relates to methods of improving form and function after traumatic injury to orbit and ocular tissues (optic nerve, retina, and uvea).

In certain embodiments, the subject is in need of treatment because of sustaining a vision threatening injury or is at risk of, suspected of having, or diagnosed with a neurological disorder glaucoma, and/or ischemic retinopathy.

In certain embodiments, this disclosure relates to methods of activating TrkB in the retina, in ganglion cells, and brain comprising administering an effective amount of an N-acetylserotonin derivative disclosed herein to a subject in need thereof.

The composition may be administered to patients in an amount effective, especially to enhance pharmacological response in an animal or human organism. As used herein, the term "effective amount" refers to an amount sufficient to realize a desired biological effect. The appropriate dosage may vary depending upon known factors such as the pharmacodynamic characteristics of the particular active agent, age, health, and weight of the host organism; the condition (s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques.

The therapeutically effective amount of a compound disclosed herein may be administered in a single dose or a dose repeated one or several times after a certain time interval. In embodiments, the therapeutically effective amount is administered daily or every two or three days, or once a week. Administration may be one, twice, or three times daily, e.g., single dose of 500 mg daily, single dose of 850 mg, 850 mg twice daily, or 850 mg three times daily, single dose of 1,000 mg daily, single dose of 100 mg daily, single dose of 200 mg, single dose of 400 mg, 100 mg twice daily, or 200 mg three times daily. In embodiments, the therapeutically effective amount is administered daily or every other day for more than two weeks, ten weeks, thirty weeks, a year, or as long as symptoms or the disease are present.

In certain embodiments, this disclosure contemplates that N-acetylserotonin derivative disclosed herein and pharmaceutical compositions comprising the same are administered topically, locally ocular (i.e., subconjunctival, intravitreal, retrobulbar, intracameral, intravitreal injections/implants and periocular injections), and/or systemically. In certain embodiments, this disclosure contemplates administration as a cream, an ointment, or a liquid drop preparation in the conjunctival sac. In certain embodiments, this disclosure contemplates systemic or oral delivery alone or in combination with topical delivery.

In embodiments, the methods may include the co-administration of a second active agent such as steroids, prednisone, triamcinolone, triamcinolone acetonide, triamcinolone furetonide, triamcinolone hexacetonide, triamcinolone diacetate, lidocaine, articaine, bupivacaine, epinephrine, and other anesthetics. In embodiments, co-administration may be part of the same pharmaceutical composition or separated pharmaceutical compositions described herein. In embodiments, co-administration may be at the same time, substantially the same time, before or after administration of the compositions described herein.

Pharmaceutical Compositions

In embodiments, an N-acetylserotonin derivative disclosed herein is in a pharmaceutical composition. In embodiments, a pharmaceutical composition of the disclosure comprises a carrier and/or diluent appropriate for its delivering by injection to a human or animal organism. Such carrier and/or diluent is non-toxic at the dosage and concentration employed. In certain embodiments, the pharmaceutical composition is an eye drop composition or an intraocular or intravenous composition.

In certain embodiments, this disclosure relates to pharmaceutical compositions comprising a therapeutically effective amount of an N-acetylserotonin derivative disclosed herein and a pharmaceutically acceptable carrier. In certain embodiments, such pharmaceutical compositions are formulated for intravenous, ocular or intra-ocular administration, oral administration, rectal administration, inhalation, nasal administration, and/or topical administration. In other embodiments, such pharmaceutical compositions are formulated as tablets, pills, capsules, a liquid, an inhalant, a nasal spray solution, a suppository, a solution, an emulsion, an ointment, eye drops or ear drops.

The pharmaceutical composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Eye drop compositions are typically an aqueous saline solution optionally containing a lubricant and/or other agents. In certain embodiments, the solution comprises a saccharide, polysaccharide, polyethylene glycol, propylene glycol, hydroxypropyl methylcellulose, carboxymethylcellulose, aminomethyl propanol, boric acid, dextran, glycerin, hypromellose, sorbitol, polysorbate, polyvinyl alcohol, povidone, polycationic polymer, preservative, benzalkonium chloride, steroids, dexamethasone, antihistamines, sympathomimetics, beta receptor blockers, parasympathomimetics, prostaglandins, nonsteroidal anti-inflammatory drugs (NSAIDs), antibiotics, a polymyxin, neomycin, antifungal, or topical anesthetic.

For parental administration, a pharmaceutical composition is typically in either unit dosage or multi-dose form or for direct infusion by continuous or periodic fusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solution, Hank's solution, and other aqueous physiologically balanced salt solutions (see for example the most current editions of Remington: The Science and Practice of Pharmacy, A. Gennaro, Lippincott, Williams & Wilkins). The pH of the composition of the disclosure is typically suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/l Tween 80, 10 mM Tris pH 8.5. Another typical composition is formulated in 10 mg/ml mannitol, 1 mg/ml HAS, 20 mM Tris, pH 7.2, and 150 mM NaCl.

The pharmaceutical composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm 51, 210-218). Representative examples of stabilizing components include polysorbate 80, L-arginine, polyvinylpyrrolidone, trehalose, and combinations thereof. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

In certain embodiments, the disclosure contemplates lipophilic acyl ester prodrugs of an N-acetylserotonin derivative disclosed herein, such as a valerate ester prodrug. See Tirucherai, J Ocul Pharmacol Ther. 2002; 18 (6): 535-548. In certain embodiments, the disclosure contemplates hydrophilic amide prodrugs of an N-acetylserotonin derivative disclosed herein, such as succinamidic acid and maleamidic acid prodrugs. See Malik, Mol Pharm. 2012; 9(3): 605-614.

In certain embodiments, this disclosure contemplates an N-acetylserotonin derivative disclosed herein contained within auto-injectors, similar to that used for intramuscular injection e.g., retractable needle or spring-loaded syringes configured such that pressing a button, the syringe needle is automatically inserted and the drug is administered, or a container of pressurized gas that propels a fine jet of liquid through the skin, and microneedles. In certain embodiments, this disclosure contemplation administration of an N-acetylserotonin derivative disclosed herein with microneedles. The microneedles may be designed to penetrate into the sclera or suprachoroidal space (SCS) and deposit an N-acetylserotonin derivative disclosed herein or pharmaceutical composition comprising the same. The depot typically facilitates diffusion into deeper ocular tissues (i.e., choroid and neural retina).

In certain embodiments, this disclosure contemplates an N-acetylserotonin derivative disclosed herein contained within or attached to dendrimers and cyclodextrins. In certain embodiments, this disclosure contemplation administration of an N-acetylserotonin derivative disclosed herein within or covalently attached to dendrimers and cyclodextrins. Examples of dendrimers include poly(amidoamine) (PAMAM) and polypropylenimine.

In certain embodiments, this disclosure contemplates an N-acetylserotonin derivative disclosed herein contained within nanoparticles, liposomes or nanomicelles. In certain embodiments, this disclosure contemplation administration of an N-acetylserotonin derivative disclosed herein contained within nanoparticles, liposomes or nanomicelles. Nanoparticles may be composed of lipids, proteins, and natural or synthetic polymeric systems. Examples include polymeric systems comprising albumin, hyaluronic acid (HA), sodium alginate, chitosan, poly(lactide-co-glycolic acid) (PLGA), poly(lactic acid) (PLA), polycaprolactone (PCL), PEG, and poly(glycolic acid) (PGA).

Nanomicelles self-assemble from amphiphilic monomers/molecules with sizes from 5 to 200 nm. Monomers tend to initiate self-aggregation. Liposomes and nanomicelles may be either prepared from surfactants (ionic, nonionic, zwitterionic) or block copolymers. Examples include sodium dodecyl sulfate, dodecyltrimethylammonium bromide, n-dodecyl tetra (ethylene oxide), and dioctanoyl phosphatidyl choline. Block copolymers. Polymer blocks may arrange in different ways. Examples include PEG, PLL, polyethylene oxide, poly(D,L-lactic acid), polypropylene oxide, PCL, PGA, and poly(amino acids), such as poly(aspartic acid), poly(glutamic acid), poly(L-lysine), and poly(histidine).

Preventing Visual Loss after Head Trauma

This disclosure contemplates pharmaceutical treatments for trauma-induced vision loss that can be administered on the battlefield or in field hospitals during the critical period before irreversible neuronal degeneration and vision loss occur. A mouse blast injury model has been used to characterize the effects of blast injury to the eye and visual system. Blast injury results in (1) inflammatory responses (microglial activation and reactive gliosis) and activation of the innate and acquired immune system; (2) loss of visual function (contrast sensitivity and visual acuity); (3) thinning of the nerve fiber layer of the retina, and (4) axon loss in the optic nerve. An N-acetylserotonin derivative, N-[2-(5-hydroxy-1H-indol-3-yl)ethyl]-2-oxopiperidine-3-carboxamide (HIOC), effectively mitigates vision loss when administered within several hours after blast exposure (FIG. 1). Daily administration for one week reduces or prevents blast-induced loss of visual function for at least 4 months, mitigating the progressive vision loss that occurs over time in the absence of treatment. This therapeutic effect of HIOC is mediated by activation of TrkB, the cognate receptor for Brain-Derived Neurotrophic Factor (BDNF). Both N-acetylserotonin and HIOC activate TrkB and have neuroprotective properties. The pharmacokinetic characteristics of HIOC are desirable for an in vivo treatment because TrkB is activated for up to 16 hours following a single injection. HIOC treatment reduces vision loss, microglial activation in the retina, nerve fiber layer thinning, and the optic nerve axon loss resulting from blast exposure.

HIOC can be administered systemically, crosses the blood-retinal and blood-brain barriers (BBB) to activate TrkB in the retina and brain. In the retina, the activation of TrkB was notably prominent in ganglion cells. HIOC has other neuroprotective effects. It reduces photoreceptor damage resulting from toxic light exposure, attenuates brain damage from subarachnoid hemorrhage, and inhibits neuronal apoptosis induced by kainic acid, a neurotoxin.

Generally, there is a need to address inadequate mitigation and treatment of damaged ocular structures and the visual system consequent to military-relevant injuries injuries and from other forma of blunt force trauma. Inadequate treatments exist for managing injuries and diseases to ocular structures and visual systems resulting in neuropathy, retinal injury, and ocular polytrauma. Thus, it is desirable to provide efficacy of treatments for returning form and function after traumatic injury to orbit and ocular tissues (optic nerve, retina, and uvea).

EXAMPLES

Effect of HIOC on TBI-Induced Loss of Visual Function

The ability of HIOC to mitigate the loss of visual function resulting from blast directed at the head was examined (FIG. 1). Mice were exposed to a single blast of ~70 psi directed on the right side of the head. Contrast sensitivity was measured 1 week after blast. HIOC (80 mg/kg) completely prevented the TBI induced decrease in contrast sensitivity (FIG. 1). Similar results were found for visual acuity.

Monomethyl Analogs of HIOC

Figure 2:
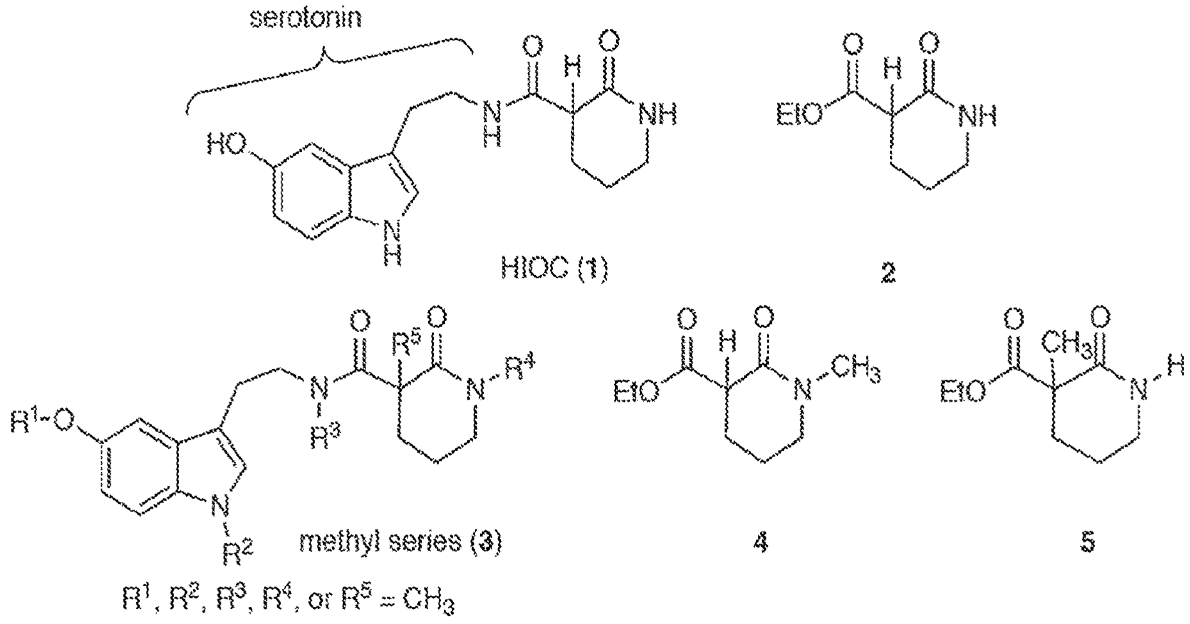
FIG. 2 illustrates N-acetylserotonin derivative disclosed herein, e.g., O—, N—, and C-alkyl derivatives of HIOC.

FIG. 2 illustrates compounds contemplated for regioselective replacement of hydrogen bond donor atoms with methyl groups. These analogs may be prepared by applying a chemoselective N-acylation method reported in Setterholm et al., Tetrahedron Lett. 2015, 56(23): 3413-3415, Nelson et al., Chiral Anion Phase Transfer of Aryldiazonium Cations: An Enantioselective Synthesis of C3-Diazenated Pyrroloindolines. *Angew. Chem. Int. Ed.* 2014, 53, 5600-5603; Xu et al., An environmentally friendly protocol for oxidative halocyclization of tryptamine and tryptophol derivatives. *Green Chem.* 2017, 19, 2952-2956); Taborsky et al., Synthesis and Preliminary Pharmacology of Some 1-Methylindoles." J. Med. Chem. 1965, 8, 460-466; Somei et al., The Chemistry of Indoles. CIII. Simple Syntheses of Serotonin, N-Methylserotonin, Bufotenine, 5-Methoxy-N-methyltryptamine, Bufobutanoic Acid, N-(Indol-3-yl)methyl-5-methoxy-N-methyltryptamine, and Lespedamine Based on 1-Hydroxyindole Chemistry. *Chem. Pharm. Bull.* 2001, 49, 87-96; Loreto et al., Novel Spiroheterocycles by Aziridination of α-Methylene-γ-and-δ-lactams. *Eur. J. Org. Chem.* 2007, 2365-2371; and Banerjee et al., An enantiodivergent synthesis of $C^{\alpha}$-methyl nipecotic acid analogues from δ-lactam derivatives obtained through a highly stereoselective cyclization strategy. *Tetrahedron: Asymmetry* 2015, 26, 1292-1299).

N-(2-(5-methoxy-1H-indol-3-yl)ethyl)-2-oxopiperidine-3-carboxamide (149)

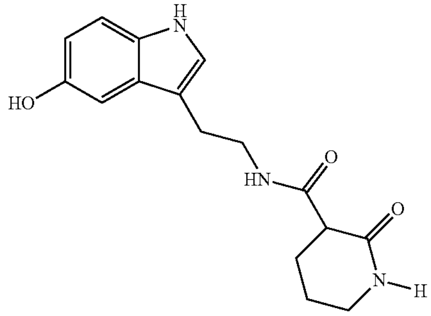

HIOC

To an oven-dried three-neck flask was added 2-oxopiperidine-3-carboxylic acid (179 mg, 1.25 mmol) and 1,1'-carbonyldiimidazole (CDI, 200 mg, 1.24 mmol, 0.99 equivalent) under argon atmosphere. Anhydrous dichloromethane (8 mL) was added, and the mixture was stirred for 30 min. 5-Methoxytryptamine hydrochloride (280 mg, 1.24 mmol, 0.99 equivalent) was added in one portion followed by anhydrous pyridine (8 mL). After 5 min a small portion of 5-Methoxytryptamine remained insoluble whereupon triethylamine (251 mg, 2.48 mmol, 2 equivalents) was added forming a homogenous solution. The reaction mixture was stirred for 12 hrs at room temperature. After 12 hrs, the reaction mixture was analyzed by thin layer chromatography (TLC, ethyl acetate:methanol (97:3) eluent, stained with p-anisaldehyde). A new purple spot corresponding to product (149) was observed. TLC indicated that 5-Methoxytryptamine hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (97:3), to which silica gel was added to adsorb the crude product. After concentration by rotary evaporation to remove the ethyl acetate, the crude product mixture adsorbed on silica gel was dry loaded onto a chromatography column, and eluted via ethyl acetate:methanol gradient. Ethyl acetate:methanol (97:3, v/v) was used to elute the least polar material, after which concentration of methanol was increased to 10%, at which product (149) began to elute and was followed by TLC analysis (97:3, v/v). The combined fractions were concentrated by rotary evaporation to yield a white solid. The desired product 149 was produced in 63% yield (248 mg).

$^1$H-NMR (600 MHz, DMSO-$d_6$): 10.61 (s, 1H), 8.03-8.02 (t, J=5.7 Hz, 1H), 7.62 (s, 1H), 7.18-7.16 (d, J=9 Hz, 1H), 7.08 (s, 1H), 6.98 (d, J=2.4 Hz, 1H), 6.67-6.65 (dd, J=2.4 Hz, 1H), 3.72 (s, 3H), 3.30-3.25 (m, 2H), 3.08 (m, 2H), 3.04-3.01 (t, J=7.2 Hz, 1H), 2.75-2.72 (t, J=7.2 Hz, 2H), 1.87-1.86 (m, 1H), 1.78-1.74 (m, 2H), 1.54-1.49 (m, 1H).

$^{13}$C-NMR: 170.1, 168.7, 153.4, 131.8, 127.9, 123.8, 112.4, 111.9, 111.5, 100.5, 55.8, 48.4, 41.8, 40.3, 25.5, 24.9.

HRMS: $C_{17}H_{22}N_3O_3$ $[M+H]^+$ calculated 316.16557; found 316.16534

N-(2-(1H-indol-3-yl)ethyl)-2-oxopiperidine-3-carboxamide (145)

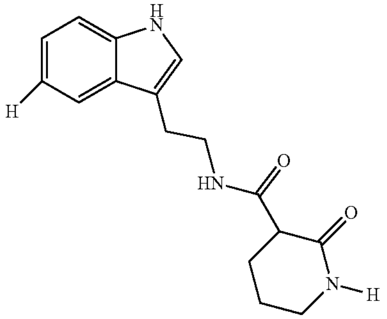 [SMILES: O=C1NCCCC1C(=O)NCCc1c[nH]c2ccccc12]

To an oven-dried three-neck flask was added 2-oxopiperidine-3-carboxylic acid (363 mg, 2.54 mmol) and 1,1'-carbonyldiimidazole (CDI, 407 mg, 2.51 mmol, 0.99 equivalent) under argon atmosphere. Anhydrous dichloromethane (8 mL) was added, and the mixture was stirred for 30 min. Tryptamine hydrochloride (494 mg, 2.51 mmol, 0.99 equivalent) was added in one portion followed by anhydrous pyridine (8 mL). After 15 min complete dissolution of tryptamine hydrochloride was observed. Triethylamine (514 mg, 5.08 mmol, 2 equivalent) was added, and the reaction mixture was stirred for 12 hrs at room temperature, after which time TLC analysis (ethyl acetate:methanol (95:5) eluent, stained with p-anisaldehyde) revealed that tryptamine hydrochloride was consumed, and a new purple spot corresponding to product (145) was observed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (95:5), to which silica gel was added to adsorb the crude product. After concentration by rotary evaporation to remove the ethyl acetate, the crude product mixture adsorbed on silica gel was dry loaded onto a chromatography column, and eluted via ethyl acetate:methanol (95:5, v/v) as followed by TLC analysis. The combined fractions were concentrated by rotary evaporation to yield a white solid. The desired product 145 was produced in 37% yield (267 mg).

$^1$H-NMR (600 MHz, DMSO-$d_6$): 10.78 (s, 1H), 8.07-8.05 (t, J=5.0 Hz, 1H), 7.64 (s, 1H), 7.51-7.50 (d, J=8.2 Hz, 1H), 7.30-7.29 (d, J=7.62, Hz, 1H), 7.13 (s, 1H), 7.03-7.01 (t, J=7.61 Hz, 1H), 6.94-6.92 (t, J=7.32 Hz, 1H), 3.30-3.25 (m, 2H), 3.08 (s, 2H), 3.05-3.02 (t, J=7.03 Hz, 1H), 2.79-2.77 (t, J=7.03 Hz, 2H), 1.90-1.85 (m, 1H), 1.78-1.73 (m, 2H), 1.53-1.50 (m, 1H).

HRMS: $C_{16}H_{19}N_3O_3$ $[M+H]^+$ calculated 286.15500; found 286.15457

N-(2-(5-methoxy-1H-indol-3-yl)ethyl)-2-oxopiperidine-3-carboxamide (149)

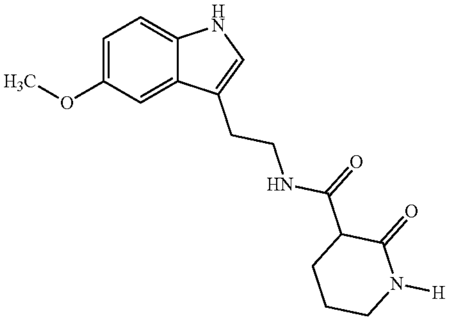 [SMILES: COc1ccc2[nH]cc(CCNC(=O)C3CCCNC3=O)c2c1]

To an oven-dried three-neck flask was added 2-oxopiperidine-3-carboxylic acid (179 mg, 1.25 mmol) and 1,1'-carbonyldiimidazole (CDI, 200 mg, 1.24 mmol, 0.99 equivalent) under argon atmosphere. Anhydrous dichloromethane (8 mL) was added, and the mixture was stirred for 30 min. 5-Methoxytryptamine hydrochloride (280 mg, 1.24 mmol, 0.99 equivalent) was added in one portion followed by anhydrous pyridine (8 mL). After 5 min a small portion of 5-Methoxytryptamine remained insoluble whereupon triethylamine (251 mg, 2.48 mmol, 2 equivalents) was added forming a homogenous solution. The reaction mixture was stirred for 12 hrs at room temperature. After 12 hrs, the reaction mixture was analyzed by thin layer chromatography (TLC, ethyl acetate:methanol (97:3) eluent, stained with p-anisaldehyde). A new purple spot corresponding to product (149) was observed. TLC indicated that 5-Methoxytryptamine hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (97:3), to which silica gel was added to adsorb the crude product. After concentration by rotary evaporation to remove the ethyl acetate, the crude product mixture adsorbed on silica gel was dry loaded onto a chromatography column, and eluted via ethyl acetate:methanol gradient. Ethyl acetate:methanol (97:3, v/v) was used to elute the least polar material, after which concentration of methanol was increased to 10%, at which product (149) began to elute and was followed by TLC analysis (97:3, v/v). The combined fractions were concentrated by rotary evaporation to yield a white solid. The desired product 149 was produced in 63% yield (248 mg).

$^1$H-NMR (600 MHz, DMSO-$d_6$): 10.61 (s, 1H), 8.03-8.02 (t, J=5.7 Hz, 1H), 7.62 (s, 1H), 7.18-7.16 (d, J=9 Hz, 1H), 7.08 (s, 1H), 6.98 (d, J=2.4 Hz, 1H), 6.67-6.65 (dd, J=2.4 Hz, 1H), 3.72 (s, 3H), 3.30-3.25 (m, 2H), 3.08 (m, 2H), 3.04-3.01 (t, J=7.2 Hz, 1H), 2.75-2.72 (t, J=7.2 Hz, 2H), 1.87-1.86 (m, 1H), 1.78-1.74 (m, 2H), 1.54-1.49 (m, 1H).

$^{13}$C-NMR: 170.1, 168.7, 153.4, 131.8, 127.9, 123.8, 112.4, 111.9, 111.5, 100.5, 55.8, 48.4, 41.8, 40.3, 25.5, 24.9.

HRMS: $C_{17}H_{22}N_3O_3$ $[M+H]^+$ calculated 316.16557; found 316.16534

N-(2-(5-hydroxy-1H-indol-3-yl)ethyl)-1-methyl-2-oxopiperidine-3-carboxamide (151)

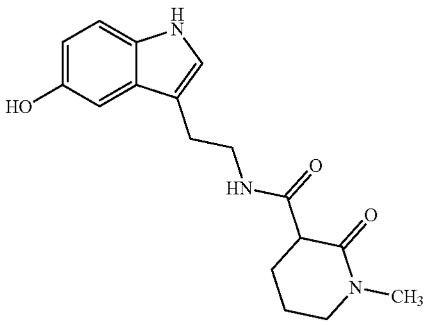 [SMILES: CN1CCCC(C(=O)NCCc2c[nH]c3ccc(O)cc23)C1=O]

To an oven-dried three-neck flask was added 1-methyl-2-oxopiperidine-3-carboxylic acid (404 mg, 2.57 mmol) and 1,1'-carbonyldiimidazole (CDI, 417 mg, 2.56 mmol, 0.99 equivalent) under argon atmosphere. Anhydrous dichloromethane (8 mL) was added, and the mixture was stirred for 30 min. Serotonin hydrochloride (547 mg, 2.56 mmol, 0.99 equivalent) was added in one portion followed by anhydrous pyridine (8 mL). After 15 min a small portion of serotonin hydrochloride remained insoluble whereupon triethylamine (520 mg, 5.14 mmol, 2 equivalents) was added forming a homogenous solution. The reaction mixture was stirred for 12 hrs at room temperature. After 12 hrs, the reaction mixture was analyzed by thin layer chromatography (TLC, ethyl acetate:methanol (98:2) eluent, stained with p-anisaldehyde). A new purple spot corresponding to product (151) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (98:2), to which silica gel was added to adsorb the crude product. After concentration by rotary evaporation to remove the ethyl acetate, the crude product mixture adsorbed on silica gel was dry loaded onto a chromatography column, and eluted via ethyl acetate:methanol gradient. Ethyl acetate:methanol (98:2, v/v) was used to elute the least polar material, after which concentration of methanol was increased to 10%, at which product (151) began to elute and was followed by TLC analysis (90:10, v/v). The combined fractions were concentrated by rotary evaporation to yield an airy white solid. The desired product 151 was produced in 26% yield (214 mg).

$^1$H-NMR (600 MHz, DMSO-$d_6$): 10.46 (s, 1H), 8.56 (s, 1H), 8.00 (t, J=Hz, 1H), 7.61 (s, 1H), 7.09-7.07 (d, J=8.4 Hz, 1H), 7.03-7.02 (d, J=1.8 Hz, 1H), 6.80-6.79 (d, J=1.8 Hz, 1H), 6.56-6.54 (dd, J=2.1 Hz, 1H), 3.28-3.19 (m, 4H), 3.10-3.08 (t, J=6.9 Hz, 1H), 2.79 (s, 3H), 2.70-2.67 (t, J=7.5 Hz, 2H), 1.93-1.91 (m, 1H), 1.84-1.80 (m, 2H), 1.66-1.63 (m, 1H).

HRMS: $C_{17}H_{22}N_3O_3$ $[M+H]^+$ calculated 316.16557; found 316.16522

N-(2-(5-hydroxy-1H-indol-3-yl)ethyl)-3-methyl-2-oxopiperidine-3-carboxamide (170)

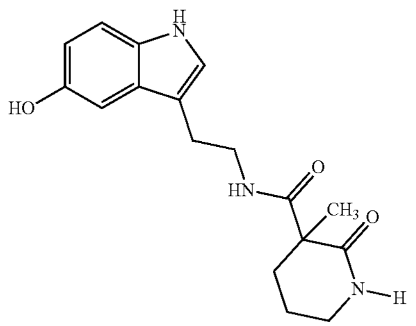 [SMILES: CC1(C(=O)NCCc2c[nH]c3ccc(O)cc23)CCCNC1=O]

To an oven-dried three-neck flask was added 3-methyl-2-oxopiperidine-3-carboxylic acid (330 mg, 2.10 mmol) and 1,1'-carbonyldiimidazole (CDI, 337 mg, 2.08 mmol, 0.99 equivalent) under argon atmosphere. Anhydrous dichloromethane (6 mL) was added, and the mixture was stirred for 90 min. Serotonin hydrochloride (446 mg, 2.09 mmol, 0.99 equivalent) was added in one portion followed by anhydrous pyridine (6 mL). After 15 min a small portion of serotonin hydrochloride remained insoluble whereupon triethylamine (424 mg, 4.19 mmol, 2 equivalents) was added forming a homogenous solution. The reaction mixture was stirred for overnight at room temperature. The reaction mixture was analyzed by thin layer chromatography (TLC, ethyl acetate:methanol (97:3) eluent, stained with p-anisaldehyde). A new purple spot corresponding to product (170) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (97:3), to which silica gel was added to adsorb the crude product. After concentration by rotary evaporation to remove the ethyl acetate, the crude product mixture adsorbed on silica gel was dry loaded onto a chromatography column, and eluted via ethyl acetate:methanol gradient. Ethyl acetate:methanol (97:3, v/v) was used to elute the least polar material, after which concentration of methanol was increased to 5%, at which product (170) began to elute and was followed by TLC analysis (95:5, v/v). The combined fractions were concentrated by rotary evaporation to yield an airy white solid. The desired product 170 was produced in 25% yield (166 mg).

$^1$H-NMR (600 MHz, DMSO-$d_6$): 10.45 (s, 1H), 8.55 (s, 1H), 7.69 (s, 1H), 7.67-7.64 (t, J=8.7, 1H), 7.09-7.06 (d, J=12.6 Hz, 1H), 6.97 (d, J=3.6 Hz, 1H), 6.82-6.81 (d, J=3.6 Hz, 1H), 6.56-6.53 (dd, J=3.6 Hz, 1H), 3.26-3.23 (m, 2H), 3.09-3.06 (t, J=4.8 Hz, 2H), 2.69-2.65 (t, J=10.8 Hz, 2H), 2.26-2.21 (m, 1H), 1.60-1.41 (m, 3H), 1.23 (s, 3H).

$^{13}$C-NMR: 173.2, 172.2, 150.6, 131.2, 128.3, 123.6, 112.0, 111.7, 111.0, 102.7, 49.2, 42.0, 40.5, 31.8, 25.6, 25.1, 19.9.

HRMS: $C_{17}H_{22}N_3O_3$ [M+H]$^+$ calculated 316.16557; found 316.16576

N-(2-(5-hydroxy-1H-indol-32-yl)ethyl)benzamide (83)

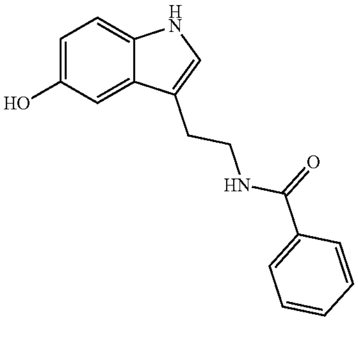 [SMILES: O=C(NCCc1c[nH]c2ccc(O)cc12)c1ccccc1]

To an oven-dried three-neck flask was benzoic acid (350 mg, 2.87 mmol) and 1,1'-carbonyldiimidazole (CDI, 460 mg, 2.84 mmol, 0.99 equivalent) under argon atmosphere. Anhydrous dichloromethane (9.5 mL) was added, and the mixture was stirred for 30 min. Serotonin hydrochloride (603 mg, 13.8 mmol, 1 equivalent) was added in one portion followed by anhydrous pyridine (9.5 mL). After 30 min the majority of serotonin hydrochloride was dissolved, however a small amount remained insoluble. Triethylamine (581 mg, 5.74 mmol, 2 equivalent) was added, and the reaction mixture was stirred for 8 hrs at room temperature. After 8 hrs, the reaction mixture was analyzed by thin layer chromatography (TLC, hexanes:ethyl acetate) (1:1) eluent, stained with p-anisaldehyde). A new purple spot corresponding to product (83), was observed. The reaction mixture was concentrated by rotary evaporation, producing a viscous oil, which was dissolved in a minimal amount of ethyl acetate, to which silica gel was added to adsorb the crude product. After concentration by rotary evaporation to remove the ethyl acetate, the crude product mixture adsorbed on silica gel was dry loaded onto a chromatography column and eluted via hexanes:ethyl acetate (1:1v/v) as followed by TLC analysis. The combined fractions were concentrated by rotary evaporation to yield a solid product 83 in 17% yield (135 mg).

$^1$H-NMR (600 MHz, DMSO-$d_6$): 10.47 (s, 1H), 8.59 (s, 1H), 8.58-8.56 (t, J=5.7 Hz, 1H), 7.83-7.82 (d, J=7.4 Hz, 2H), 7.50-7.47 (t, J=7.2, Hz, 1H), 7.44-7.42 (d, J=Hz, 2H), 7.12-7.09 (d, J=7.8 Hz, 1H), 7.05-7.04 (d, J=1.8 Hz, 1H), 6.87 (d, J=1.8 Hz, 1H), 6.58-6.56 (dd, J=2.4 Hz, 1H), 3.50-3.47 (q, J=6.6 Hz, 2H), 2.84-2.82 (t, J=7.5 Hz, 2H).

$^{13}$C-NMR: 166.5, 150.6, 135.2, 131.5, 131.2, 128.7, 128.4, 127.6, 123.5, 112.1, 111.7, 111.3, 102.7, 65.32, 40.5, 25.8.

HRMS: $C_{17}H_{17}N_2O_2$ [M+H]$^+$ calculated 281.12845; found 281.12869

N-(2-(5-hydroxy-1H-indol-3-yl)ethyl) nicotinamide (85)

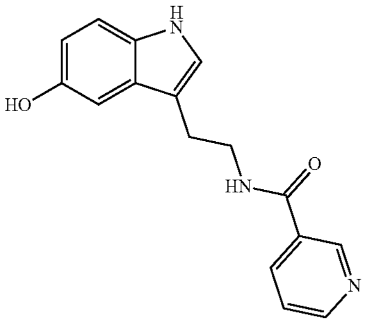 [SMILES: O=C(NCCc1c[nH]c2ccc(O)cc12)c1cccnc1]

To an oven-dried three-neck flask was added nicotinic acid (250 mg, 2.03 mmol) and 1,1'-carbonyldiimidazole (CDI, 326 mg, 2.01 mmol, 0.99 equivalent) under argon atmosphere. Anhydrous dichloromethane (7 mL) was added, and the mixture was stirred for 30 min. Serotonin hydrochloride (427 mg, 2.01 mmol, 0.99 equivalent) was added in one portion followed by anhydrous pyridine (7 mL). After 15 min a small portion of serotonin hydrochloride remained insoluble whereupon triethylamine (407 mg, 4.02 mmol, 2 equivalents) was added forming a homogenous solution. The reaction mixture was stirred for 8 hrs at room temperature. The reaction mixture was analyzed by thin layer chromatography (TLC, ethyl acetate:methanol (90:10) eluent, stained with p-anisaldehyde). A new purple spot corresponding to product (85) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate:methanol (90:10), to which silica gel was added to adsorb the crude product. After concentration by rotary evaporation to remove the ethyl acetate, the crude product mixture adsorbed on silica gel was dry loaded onto a chromatography column, and eluted via ethyl acetate: methanol (90:10) followed by TLC analysis (90:10, v/v). The combined fractions were concentrated by rotary evaporation to yield a solid. The desired product 85 was produced in 35% yield (201 mg).

$^1$H-NMR (600 MHz, DMSO-$d_6$): 10.47 (s, 1H), 8.96 (d, J=1.2 Hz, 1H), 8.77-8.75 (t, J=5.4 1H), 8.66-8.65 (d, J=4.8 Hz, 1H), 8.57 (s, 1H), 8.15-8.13 (dd, J=2.1 Hz, 1H), 7.48-7.45 (dd, J=4.8 Hz, 1H), 7.09-7.08 (d, J=8.4 Hz, 1H), 7.04 (s, 1H), 6.84 (d, J=1.8 Hz, 1H), 6.56-6.54 (dd, J=2.4 Hz, 1H), 3.50-3.48 (q, J=6.5 Hz, 2H), 2.84-2.82 (t, J=7.5 Hz, 2H).

$^{13}$C-NMR: 172.5, 165.1, 152.2, 150.6, 148.8, 135.3, 131.2, 130.6, 128.4, 123.9, 123.6, 112.1, 111.7, 111.2, 102.7, 65.3, 25.7.

HRMS: $C_{16}H_{16}N_2O_2$ $[M+H]^+$ calculated 282.12370; found 282.12400

Compounds 105 and 107 were prepared in the same manner as compound 85. Variations for purification along with characterization data is listed as follows:

N-(2-(5-hydroxy-1H-indol-3yl)ethyl) picolinamide (105)

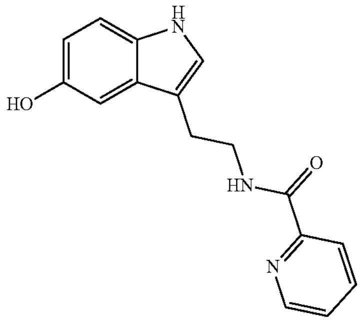 [SMILES: O=C(NCCc1c[nH]c2ccc(O)cc12)c1ccccn1]

Purification: The crude product mixture adsorbed on silica gel was dry loaded onto a chromatography column, and eluted via ethyl acetate:hexanes gradient. Ethyl acetate: hexanes (50:50, v/v) was used to elute the least polar material, after which concentration of ethyl acetate was increased to 60%, at which product (105) began to elute and was followed by TLC analysis (50:50, v/v). The combined fractions were concentrated by rotary evaporation to yield a solid. The desired product 105 was produced in 32% yield (184 mg).

$^1$H-NMR (600 MHz, DMSO-$d_6$): 10.46 (s, 1H), 8.83-8.82 (t, J=5.4 Hz, 1H), 8.59-8.58 (d, J=4.8 1H), 8.56 (s, 1H), 8.02-8.01 (d, J=8.4 Hz, 1H), 7.97-7.94 (t, J=8.4 Hz, 1H), 7.56-7.54 (dd, J=6 Hz, 1H), 7.09-7.07 (d, J=1.8 Hz, 1H), 7.04 (s, 1H), 6.87-6.86 (d, J=2.4 Hz, 1H), 6.56-6.54 (dd, J=1.8 Hz, 1H), 3.55-3.51 (q, J=7.2 Hz, 2H), 2.84-2.81 (t, J=7.5 Hz, 2H).

HRMS: $C_{16}H_{16}N_3O_2$ $[M+H]^+$ calculated 282.12370; found 282.12343

N-(2-(5-hydroxy-1H-indol-3-yl)ethyl) isonicotinamide (107)

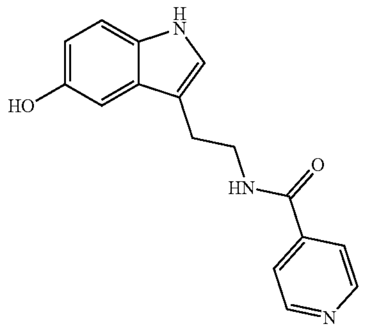 [SMILES: O=C(NCCc1c[nH]c2ccc(O)cc12)c1ccncc1]

Purification: The crude product mixture adsorbed on silica gel was dry loaded onto a chromatography column, and eluted via ethyl acetate:methanol (95:5). Fractions monitored by TLC analysis (95:5, v/v). The combined fractions were concentrated by rotary evaporation to yield a solid. The desired product 107 was produced in 36% yield (204 mg).

$^1$H-NMR (600 MHz, DMSO-$d_6$): 10.47 (s, 1H), 8.87-8.85 (t, J=5.4 Hz, 1H), 8.69-8.68 (d, J=5.4 2H), 8.57 (s, 1H), 7.72-7.71 (d, J=6 Hz, 2H), 7.09-7.08 (d, J=9 Hz, 1H), 7.04 (s, 1H), 6.84 (s, 1H) 6.56-6.55 (d, J=6.6 Hz, 1H), 3.49-3.46 (q, J=7.2 Hz, 2H), 2.84-2.81 (t, J=7.5 Hz, 2H).

HRMS: $C_{16}H_{16}N_3O_2$ $[M+H]^+$ calculated 282.12370; found 282.12334

5-fluoro-N-(2-(5-hydroxy-1H-indol-3yl)ethyl) picolinamide (112)

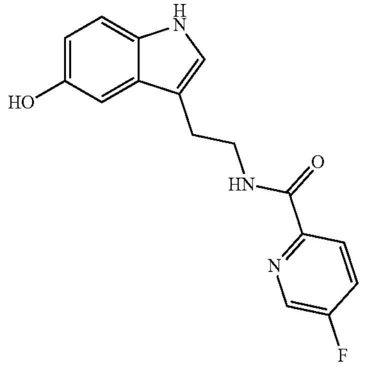 [SMILES: O=C(NCCc1c[nH]c2ccc(O)cc12)c1ccc(F)cn1]

To an oven-dried three-neck flask was added 5-fluoro-2-pyridine carboxylic acid (250 mg, 1.77 mmol) and 1,1'-carbonyldiimidazole (CDI, 284 mg, 1.75 mmol, 0.99 equivalent) under argon atmosphere. Anhydrous dichloromethane (5.5 mL) was added, and the mixture was stirred for 30 min. Serotonin hydrochloride (373 mg, 1.75 mmol, 0.99 equivalent) was added in one portion followed by anhydrous pyridine (5.5 mL). After 10 mins complete dissolution of serotonin hydrochloride was observed whereupon triethylamine (358 mg, 3.54 mmol, 2 equivalents) was added. The reaction mixture was stirred for 19 hrs at room temperature. The reaction mixture was analyzed by thin layer chromatography (TLC, hexanes:ethyl acetate (50:50) eluent, stained with p-anisaldehyde). A new purple spot corresponding to product (112) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, upon standing a yellow precipitate begun to form in the organic layer which was redissolved by addition of 5 mL of methanol and the organic layer was dried using anhydrous sodium sulfate ($Na_2SO_4$). After filtration, the organic layer was concentrated by rotary evaporation, producing a viscous oil, which was dissolved in a minimal amount of ethyl acetate, to which silica gel was added to adsorb the crude product. After concentration by rotary evaporation to remove the ethyl acetate, the crude product mixture adsorbed on silica gel was dry loaded onto a chromatography column and eluted via hexanes:ethyl acetate gradient. Hexanes: ethyl acetate (50:50, v/v) was used to elute the least polar material, after which concentration of ethyl acetate was increased to 60%, at which product (112) began to elute and was followed by TLC analysis (50:50, v/v). The combined fractions were concentrated by rotary evaporation to yield a solid. The desired product 112 was produced in 42% yield (224 mg).

$^1$H-NMR (600 MHz, DMSO-$d_6$): 10.44 (s, 1H), 8.80-8.78 (t, J=6 Hz, 1H), 8.58 (s, 1H), 8.55 (d, J=1.8 Hz, 1H), 8.09-8.06 (m, 1H), 7.88-7.85 (t, J=7.2 Hz, 1H), 7.08-7.06 (d, J=9.6 Hz, 1H), 7.03 (s, 1H) 6.85 (s, 1H), 6.55-6.53 (d, J=6.6 Hz, 1H), 3.52-3.49 (q, J=6.6 Hz, 2H), 2.82-2.80 (t, J=7.2 Hz, 2H).

HRMS: $C_{16}H_{15}N_3O_2F$ $[M+H]^+$ calculated 300.11428; found 300.11396

3-fluoro-N-(2-(5-hydroxy-1H-indol-3-yl)ethyl) isonicotinamide (114)

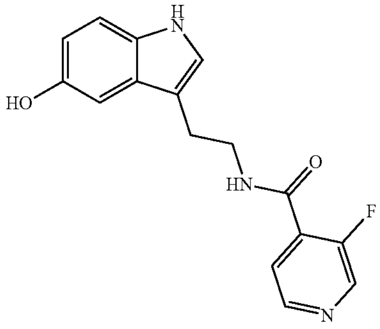 [SMILES: O=C(NCCc1c[nH]c2ccc(O)cc12)c1ccncc1F]

To an oven-dried three-neck flask was added 3-Fluoro-4-pyridine carboxylic acid (250 mg, 1.77 mmol) and 1,1'-carbonyldiimidazole (CDI, 284 mg, 1.75 mmol, 0.99 equivalent) under argon atmosphere. Anhydrous dichloromethane (5.5 mL) was added, and the mixture was stirred for 30 min. Serotonin hydrochloride (373 mg, 1.75 mmol, 0.99 equivalent) was added in one portion followed by anhydrous pyridine (5.5 mL). After 10 min, complete dissolution of serotonin hydrochloride was observed whereupon triethylamine (358 mg, 3.54 mmol, 2 equivalents) was added. The reaction mixture was stirred for 12 hrs at room temperature. The reaction mixture was analyzed by thin layer chromatography (TLC, hexanes:ethyl acetate (40:60) eluent, stained with p-anisaldehyde). A new purple spot corresponding to product (114) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate, to which silica gel was added to adsorb the crude product. After concentration by rotary evaporation to remove the ethyl acetate, the crude product mixture adsorbed on silica gel was dry loaded onto a chromatography column and eluted via hexanes:ethyl acetate gradient. Hexanes:ethyl acetate (40:60, v/v) was used to elute the least polar material, after which concentration of ethyl acetate was increased to 70%, at which remaining non-polar material was eluted, product (114) began to elute at 80% ethyl acetate and was followed by TLC analysis (40:60, hexane:ethyl acetate, v/v). The combined fractions were concentrated by rotary evaporation to yield a solid. The desired product 114 was produced in 32% yield (169 mg).

$^1$H-NMR (600 MHz, DMSO-$d_6$): 10.48 (s, 1H), 8.71 (s, 1H), 8.64 (s, 1H), 8.59 (s, 1H), 8.48-8.47 (d, J=3.6 Hz, 1H), 7.53-7.52 (t, J=5.1 Hz, 1H), 7.10-7.09 (d, J=8.4 Hz, 1H), 7.05 (s, 1H) 6.89 (s, 1H), 6.57-6.56 (d, J=6.6 Hz, 1H), 3.48-3.45 (q, J=5.3 Hz, 2H), 2.83-2.81 (t, J=7.2 Hz, 2H).

HRMS: $C_{16}H_{15}N_3O_2F$ $[M+H]^+$ calculated 300.11428; found 300.11400

5-Fluoro-N-(2-(5-hydroxy-1H-indol-3-yl)ethyl) nicotinamide (127)

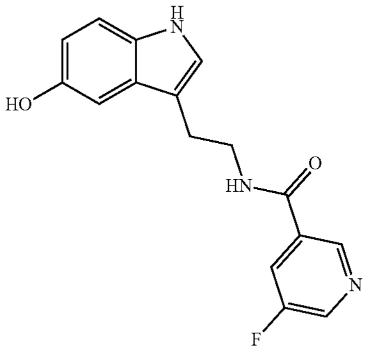 [SMILES: O=C(NCCc1c[nH]c2ccc(O)cc12)c1cncc(F)c1]

To an oven-dried three-neck flask was added 5-Fluoro-3-pyridine carboxylic acid (300 mg, 2.13 mmol) and 1,1'-carbonyldiimidazole (CDI, 341 mg, 2.10 mmol, 0.99 equivalent) under argon atmosphere. Anhydrous dichloromethane (6.5 mL) was added, and the mixture was stirred for 30 min. Serotonin hydrochloride (452 mg, 2.10 mmol, 0.99 equivalent) was added in one portion followed by anhydrous pyridine (6.5 mL). After 10 mins complete dissolution of serotonin hydrochloride was observed whereupon triethylamine (430 mg, 4.25 mmol, 2 equivalents) was added. The reaction mixture was stirred for 12 hrs at room temperature. The reaction mixture was analyzed by thin layer chromatography (TLC, hexanes:ethyl acetate (40:60) eluent, stained with p-anisaldehyde). A new purple spot corresponding to product (127) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, upon standing a precipitate begun to form in the organic layer which was redissolved by addition of 5 mL of methanol and the organic layer was dried using anhydrous sodium sulfate ($Na_2SO_4$). After filtration, the organic layer was concentrated by rotary evaporation, producing a viscous oil, which was dissolved in a minimal amount of ethyl acetate, to which silica gel was added to adsorb the crude product. After concentration by rotary evaporation to remove the ethyl acetate, the crude product mixture adsorbed on silica gel was dry loaded onto a chromatography column, and eluted via hexanes:ethyl acetate gradient. Hexanes: ethyl acetate (40:60, v/v) was used to elute the least polar material, after which concentration of ethyl acetate was increased to 70%, at which remaining non-polar material was eluted, product (127) began to elute at 80% ethyl acetate and was followed by TLC analysis (40:60, hexane:ethyl acetate, v/v). The combined fractions were concentrated by rotary evaporation to yield a solid. The desired product 127 was produced in 25% yield (159 mg).

$^1$H-NMR (600 MHz, DMSO-$d_6$): 10.47 (s, 1H), 8.85 (s, 1H), 8.70-8.69 (d, J=2.4 Hz, 1H), 8.58 (s, 1H), 8.03-8.02 (d, J=9.6 Hz, 1H), 7.10-7.09 (d, J=8.4 Hz, 1H), 7.05 (s, 1H), 6.84 (s, 1H) 6.57-6.56 (d, J=7.8 Hz, 1H), 3.51-3.48 (q, J=6.6 Hz, 2H), 2.85-2.83 (t, J=7.5 Hz, 2H).

HRMS: $C_{16}H_{15}N_3O_2F$ $[M+H]^+$ calculated 300.11428; found 300.11398

2-fluoro-N-(2-(5-hydroxy-1H-indol-3yl)ethyl) nicotinamide (147)

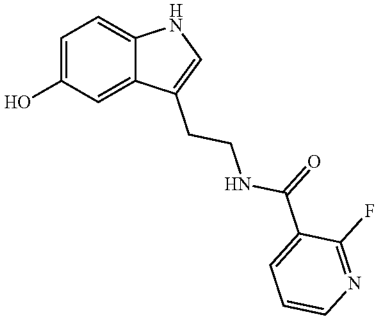 [SMILES: O=C(NCCc1c[nH]c2ccc(O)cc12)c1cccnc1F]

To an oven-dried three-neck flask was added 2-flouronicotinic acid (401 mg, 2.84 mmol) and 1,1'-carbonyldiimidazole (CDI, 460 mg, 2.84 mmol, 1 equivalent) under argon atmosphere. Anhydrous dichloromethane (8 mL) was added, and the mixture was stirred for 30 min. Serotonin hydrochloride (604 mg, 2.84 mmol, 1 equivalent) was added in one portion followed by anhydrous pyridine (8 mL). After 10 mins complete dissolution of serotonin hydrochloride was observed whereupon triethylamine (575 mg, 5.68 mmol, 2 equivalents) was added. The reaction mixture was stirred for 12 hrs at room temperature. The reaction mixture was analyzed by thin layer chromatography (TLC, hexanes: ethyl acetate (40:60) eluent, stained with p-anisaldehyde). A new purple spot corresponding to product (147) was observed. TLC indicated that serotonin hydrochloride was consumed. To the reaction mixture was added water (3 mL) and the mixture was transferred to a separatory funnel. After shaking, the heavier dichloromethane (organic) phase was separated from the lighter aqueous phase. In a separatory funnel, the organic phase was then washed with 5% (w/v) sodium bicarbonate solution (2 mL) with shaking and venting, and the process was repeated 3 times. The aqueous layer was removed, and the organic phase was then washed once with water (2 mL). The organic phase was washed with 5% acetic acid solution (2 mL) with shaking and venting, repeating the process 3 times. After separating the organic phase from the aqueous phase, the organic phase was then washed with water (2 mL). The organic layer was subsequently washed with 0.5 M aqueous HCl (2 mL) in the separatory funnel with shaking and venting, the process was repeated 3 times. After separating the aqueous phase, the organic phase was washed with 1M aqueous HCl (2 mL), and this process was repeated 3 times. Lastly the organic layer was washed with water (2 mL) followed by a brine wash (5 mL). The aqueous layer was removed, and the organic layer was dried using anhydrous sodium sulfate ($Na_2SO_4$). After filtration, the organic layer was concentrated by rotary evaporation, producing a viscous oil, which was dissolved in a minimal amount of ethyl acetate, to which silica gel was added to adsorb the crude product. After concentration by rotary evaporation to remove the ethyl acetate, the crude product mixture adsorbed on silica gel was dry loaded onto a chromatography column and eluted via hexanes:ethyl acetate gradient. Hexanes:ethyl acetate (30:70, v/v) was used to elute the least polar material, after which concentration of ethyl acetate was increased to 80%, at which product (147) began to elute and was followed by TLC analysis (40:60, hexane:ethyl acetate, v/v). The combined fractions were concentrated by rotary evaporation to yield a solid. The desired product 147 was produced in 27% yield (232 mg).

$^1$H-NMR (600 MHz, DMSO-$d_6$): 10.47 (s, 1H), 8.57 (s, 2H), 8.30-8.29 (d, J=6 Hz, 1H), 8.12-8.09 (t, J=9 Hz, 1H), 7.42-7.40 (t, J=6 Hz, 1H), 7.08-7.07 (d, J=6 Hz, 1H), 7.05 (s, 1H) 6.83-6.82 (d, J=6 Hz, 1H), 6.56-6.54 (dd, J=6 Hz, 1H), 3.47-3.43 (q, J=9 Hz, 2H), 2.82-2.79 (t, J=9 Hz, 2H).

HRMS: $C_{16}H_{15}N_3O_2F$ $[M+H]^+$ calculated 300.11428; found 300.11395

Biological Activity

Figure 5:
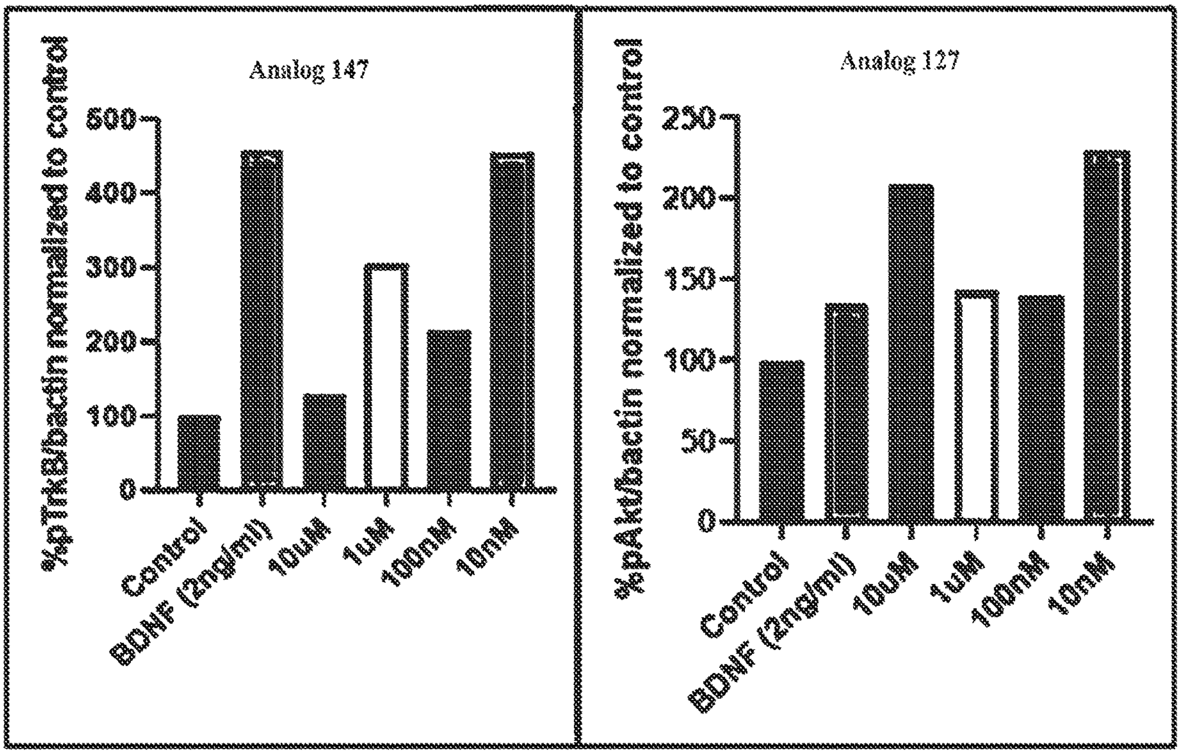
FIG. 5 shows data for an embodiment of this disclosure. Different concentrations of 2-fluoro-N-(2-(5-hydroxy-1H-indol-3-yl)ethyl) nicotinamide (analogue 147) were tested in NIH-3T3-TrkB cells. Cells at 70-80% confluency were serum deprived overnight and then stimulated with different concentrations of analogue 147 for 30 minutes. Protein extract was collected and subjected for western blot analysis. Both Analogue 147 and Analogue 127 have higher activity at low nanomolar concentrations than at 1 μM. Analogue 147 showed best TrkB activation at 10 nM (left) while Analogue 127 has a better response at 100 nM concentration (right). *Samples in lines 1-14 were tested in primary rat cortical neuronal culture. **Samples in lines 17-27 were tested in cultured NIH 3T3 cells that express human TrkB. "+"=increased phosphorylation; "–"=decreased phosphorylation; "nc"=no change.

To screen the analogs for biological activity, the phosphorylation state of TrkB and AKT, a downstream signaling mediator of TrkB activation, was examined in cultured NIH/3T3 cells expressing human TrkB and in primary cultures of rat cortical neurons (see FIG. 5).

| S. No. | Analogue ID | pTrkB/β-actin | pAkt/β-actin |
|---|---|---|---|
| Tested in rat cortical neurons | | | |
| 1. | BDNF* | + | + |
| 2. | HIOC* | + | + |
| 3. | 147* | + | + |
| 4. | 127* | + | + |
| 5. | 85* | + | + |
| 6. | 83* | + | + |
| 7. | 105* | + | + |
| 8. | 107* | + | + |
| 9. | 112* | + | − |
| 10. | 170* | + | nc |
| 11. | 149* | + | + |
| 12. | 151* | + | − |
| 13. | 145* | + | + |
| 14. | 114* | nc | nc |
| Tested in NIH 3T3 - TrkB cells | | | |
| 15. | BDNF** | + | + |
| 16. | HIOC** | + | + |
| 17. | 147** | + | + |
| 18. | 127** | + | − |
| 10. | 85** | nc | nc |
| 20. | 83** | + | + |
| 21. | 105** | − | + |
| 22. | 107** | + | + |
| 23. | 149** | − | + |
| 24. | 170** | + | + |
| 25. | 145** | + | + |

What is claimed is:

1. A compound comprising: 2-fluoro-N-(2-(5-hydroxy-1H-indol-3-yl)ethyl)nicotinamide or salt thereof.

2. A pharmaceutical composition comprising 2-fluoro-N-(2-(5-hydroxy-1H-indol-3-yl)ethyl)nicotinamide or salt thereof a pharmaceutically acceptable carrier.

3. A method of treating vision loss comprising administering an effective amount of 2-fluoro-N-(2-(5-hydroxy-1H-indol-3-yl)ethyl)nicotinamide or salt thereof to a subject that has experienced a physical impact to the head or the eye.

* * * * *